(12) United States Patent
Pianca et al.

(10) Patent No.: US 8,886,335 B2
(45) Date of Patent: Nov. 11, 2014

(54) IMPLANTABLE LEADS WITH A LOW PROFILE DISTAL PORTION

(71) Applicant: Boston Scientific Neuromodulation Corporation, Valencia, CA (US)

(72) Inventors: Anne Margaret Pianca, Santa Monica, CA (US); Jacob Matthew Muhleman, Canandalgua, NY (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/707,371

(22) Filed: Dec. 6, 2012

(65) Prior Publication Data

US 2013/0150933 A1 Jun. 13, 2013

Related U.S. Application Data

(60) Provisional application No. 61/567,789, filed on Dec. 7, 2011.

(51) Int. Cl.
*A61N 1/05* (2006.01)

(52) U.S. Cl.
CPC .............. *A61N 1/05* (2013.01); *A61N 1/0534* (2013.01)
USPC ...................................................... 607/115

(58) Field of Classification Search
CPC . A61N 1/0476; A61N 1/0488; A61N 1/0551; A61N 1/0553
USPC ................................ 607/116, 128
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,721,604 B1 * | 4/2004 | Robinson et al. ............. 607/116 |
| 6,741,892 B1 | 5/2004 | Meadows et al. |
| 7,244,150 B1 | 7/2007 | Brase et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 2002/0022873 A1 * | 2/2002 | Erickson et al. ............. 607/117 |
| 2005/0165465 A1 | 7/2005 | Pianca et al. |
| 2005/0203602 A1 * | 9/2005 | Wallace et al. ............... 607/122 |
| 2007/0150036 A1 | 6/2007 | Anderson |
| 2010/0268298 A1 | 10/2010 | Moffitt et al. |

(Continued)

*Primary Examiner* — Paula J Stice
(74) *Attorney, Agent, or Firm* — Lowe Graham Jones PLLC; Bruce E. Black

(57) ABSTRACT

A stimulation lead includes an elongate body having a proximal portion and a distal portion and has a multilumen tube extending along the elongate body and defining a central lumen and a plurality of peripheral lumens disposed circumferentially around the central lumen; a plurality of conductors, at least one of the conductors extending along the central lumen and a remainder of the conductors extending along the plurality of peripheral lumens with at least one of the conductors in each peripheral lumen; a plurality of terminals disposed along the proximal portion of the elongate body and electrically coupled to proximal ends of the conductors; and a plurality of electrodes disposed along the distal portion of the elongate body and electrically coupled to distal ends of the conductors. Each of the conductors is coupled to at least one terminal and at least one electrode.

16 Claims, 7 Drawing Sheets

(56) References Cited

U.S. PATENT DOCUMENTS

| | | |
|---|---|---|
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203320 A1 | 8/2012 | DiGiore et al. |
| 2012/0203321 A1 | 8/2012 | Moffitt et al. |

* cited by examiner

IMPLANTABLE LEADS WITH A LOW PROFILE DISTAL PORTION

CROSS-REFERENCE TO RELATED APPLICATIONS

This application claims the benefit under 35 U.S.C. §119(e) of U.S. Provisional Patent Application Ser. No. 61/567,789 filed on Dec. 7, 2011, which is incorporated herein by reference.

FIELD OF THE INVENTION

The present invention is directed to the area of implantable electrical stimulation systems and methods of making and using the systems. The present invention is also directed to implantable electrical stimulation leads having reduced diameter.

BACKGROUND OF THE INVENTION

Implantable electrical stimulation systems have proven therapeutic in a variety of diseases and disorders. For example, stimulation systems may be employed in the spinal cord to treat chronic pain syndromes and in the brain to treat refractory chronic pain syndromes, movement disorders, and epilepsy. Similarly, stimulation systems employed peripherally may prove beneficial for the treatment of chronic pain syndrome and incontinence. In some instances, functionality may return to paralyzed extremities in spinal cord injury patients by electrical stimulation. Moreover, electrical stimulation systems may be implanted subcutaneously to stimulate subcutaneous tissue including subcutaneous nerves such as the occipital nerve, and the trigeminal nerve.

Though these stimulation systems vary in design, they include the same core elements—a control module (with a pulse generator), one or more leads, and an array of stimulator electrodes on each lead. The stimulator electrodes are placed in contact with or near the nerves, muscles, or other tissue to be stimulated. The pulse generator in the control module generates electrical pulses that are delivered through the lead and the electrodes to body tissue.

Target areas may include the face (facial nerves such as the trigeminal nerves), the skull, or limbs. For peripheral and subcutaneous target areas in thin patients, standard diameter leads may not be suitable. Similarly, for deep brain stimulation, where a cannula is passed through a tract in the brain, smaller leads may be more beneficial as they displace less brain tissue, minimizing potential irreparable damage.

SUMMARY OF THE INVENTION

One embodiment is a stimulation lead having an elongate body with a proximal portion and a distal portion and including a multilumen tube extending along the elongate body and defining a central lumen and a plurality of peripheral lumens disposed circumferentially around the central lumen; a plurality of conductors, at least one of the conductors extending along the central lumen and a remainder of the conductors extending along the plurality of peripheral lumens with at least one of the conductors in each peripheral lumen; a plurality of terminals disposed along the proximal portion of the elongate body, each of the terminals electrically coupled to a proximal end of a one of the plurality of conductors; and a plurality of electrodes disposed along the distal portion of the elongate body, each of the electrodes electrically coupled to a distal end of a one of the plurality of conductors. Each of the conductors is coupled to at least one terminal and at least one electrode.

Another embodiment is a method of making a stimulation lead. The method includes extruding a multilumen tube with a plurality of conductors extending along the tube; disposing a plurality of electrodes along a distal portion of the tube and electrically coupling the electrodes to the plurality of conductors; and disposing a plurality of terminals along a proximal portion of the tube and electrically coupling the terminals to the plurality of conductors.

A further embodiment is a stimulation lead including an elongate body having a proximal portion and a distal portion and including an insulative core extending from the proximal portion to the distal portion; at least eight conductors extending along the elongate body and collectively wrapped around the insulative core, the conductors being electrically insulated from each other; a plurality of terminals disposed along the proximal portion of the elongate body, the terminals electrically coupled the plurality of conductors; and a plurality of electrodes disposed along the distal portion of the elongate body, the electrodes electrically coupled to the plurality of conductors. Each conductor is coupled to at least one terminal and at least one electrode. A diameter of the lead is no more than 0.039" along at least a portion of the lead containing the electrodes.

Yet another embodiment is a stimulation lead including an elongate body having a proximal end and a distal end and having a multilumen tube extending along the elongate body and defining a plurality of lumens; a plurality of conductors, each conductor extending along a one of the plurality of lumens; a plurality of terminals disposed on the proximal end of the elongate body, the terminals electrically coupled to a proximal end of a one of the plurality of conductors; and a plurality of electrodes disposed on the distal end of the elongate body, the electrodes electrically coupled to a distal end of a one of the plurality of conductors. An outer diameter of the lead is no more than 0.039" along at least a portion of the lead containing the electrodes.

Another embodiment is a stimulation lead including an elongate body having a proximal portion and a distal portion. The proximal portion has a circular lateral cross-section with a diameter and the distal portion includes a low-profile region having a non-circular lateral cross-section with a diameter in at least one direction that is at least 10% less than the diameter of the circular cross-section. The stimulation lead also includes a plurality of terminals disposed along the proximal portion of the elongate body; a plurality of electrodes disposed along the distal portion of the elongate body with at least one of the electrodes disposed in the low-profile region; and a plurality of conductors coupling the plurality of terminals to the plurality of electrodes. The diameter of the non-circular cross-section is no more than 0.039"

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DESCRIPTION OF THE EMBODIMENTS

The present disclosure is directed to the area of implantable electrical stimulation systems and methods of making and using the systems. The disclosure is also directed to implantable electrical stimulation leads with diameters relatively smaller than standard leads. Further, the present disclosure describes methods of manufacturing such reduced diameter leads.

Suitable implantable electrical stimulation systems include, but are not limited to, an electrode ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are present in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710 and U.S. Patent Application Publications Nos. 2005/0165465 and 2007/0150036, all of which are incorporated by reference.

Many conventional stimulation systems utilize leads with diameters in the range of 0.050" to 0.056" (about 1.27 to 1.42 mm) or more. Although these leads may not pose problems for spinal cord stimulation, they may not be suitable for target areas where the tissue above the lead is very thin. These target areas may include the face (facial nerves such as the trigeminal nerves), the skull, or limbs. Moreover, for peripheral and subcutaneous target areas in thin patients, standard diameter leads may not be suitable. Similarly, for deep brain stimulation, where a cannula is passed through a tract in the brain, small diameter leads may be more beneficial as they displace less brain tissue, reducing potential irreparable damage.

Figure 1:
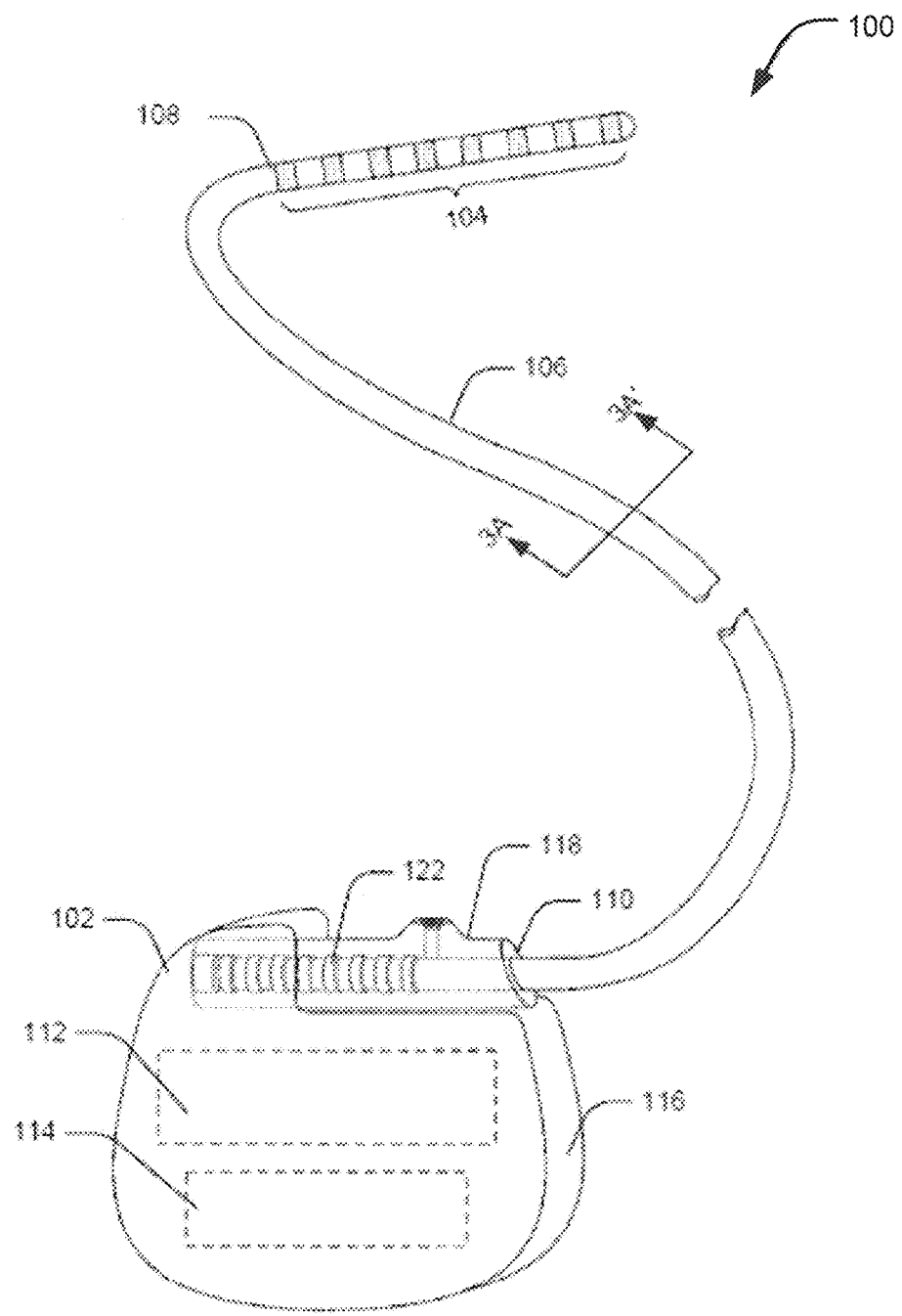
FIG. 1 is a schematic perspective view of a stimulation system, according to the invention.

FIG. 1 illustrates an exemplary electrical stimulation system 100 adapted to perform a desired procedure. Electrical stimulation system 100 includes a control module 102, such as a stimulator or pulse generator, a plurality of electrodes 104, and at least one lead 106 coupling the plurality of electrodes to the control module. The electrodes may be disposed at the distal end 108 of the lead, while the control module 102 may be connected to the lead's proximal end 110. Throughout this disclosure, the term "distal" refers to the end away from the control module, while the term "proximal" refers to the end toward the control module.

One or more components of the stimulation system 100 are typically implanted into a patient's body for a variety of applications including, but not limited to, brain stimulation, neural stimulation, spinal cord stimulation, or muscle stimulation. For example, a portion of the lead 106 and the electrodes 104 may be implanted in the patient's body, contacting or near the target region, and the pulse generator may be present outside the patient's body, for example strapped to the patient's arm, wrist, or taped around her chest. Alternatively, the entire stimulation system 100 may be implanted in the patient's body. The electrodes 104 may be implanted at the target area, and the control module 102 may be implanted in any suitable area within the body large enough to accommodate it, such as the abdominal cavity.

The control module 102 typically includes an electronic subassembly 112 and an optional power source 114 disposed in a sealed housing 116. This module also includes a connector 118 into which the proximal end 110 of the lead 106 can be plugged to make an electrical connection via conductive contacts (not shown) on the control module 102 and terminals 122 on each lead 106. Optionally, one or more lead extensions (not shown) can connect lead 106 and control module 102 to extend the distance between those elements. When the control module 102 is implanted at a distance from the target area or left outside the patient's body, one or more lead extensions may be utilized to increase the length of the leads.

The control module 102 generates electrical impulses, which are provided to the electrodes 104 through the lead 106. These electrical impulses can stimulate the target nerve, muscle, or organ. In some embodiments, physicians or operators may regulate or modify the strength (amplitude), duration (pulsewidth), and period (frequency) between stimulus pulses using a remote controller (not shown). The controller may be external to the patient's body and may communicate with the control module 102 wirelessly.

The electrodes 104 may be configured in any arrangement at the distal end of the lead. One configuration commonly used in percutaneous stimulation, depicted in FIG. 1, includes multiple electrodes circumferentially positioned along the distal portion of the elongate lead. Invasive surgical procedure may not be required to implant the lead. For example, the lead, along with the electrode array, may be placed through an epidural-type needle, reducing surgical trauma.

In another configuration, the electrodes may be placed on a paddle, which has a multiplicity of electrode contacts spread out over a flat, paddle-like surface that is disposed at the distal end 108 of the lead. A paddle lead permits the electrode contacts to be spaced apart to provide wide coverage over a stimulation area. In at least some embodiment, the paddle lead may be implanted via a laminectomy.

Electrodes can be formed using any conductive, biocompatible material. Examples of suitable material include metals, alloys, conductive polymers, and conductive carbon. The number of electrodes in the electrode array may vary depending on the target area, and the condition being treated. For example, there may be two, four, six, eight, ten, twelve, fourteen, sixteen, or more electrode. As will be recognized, other numbers of electrodes are also contemplated.

Generally, the lead 106 is an elongate member having a distal end 108 and a proximal end 110. The proximal end 110 may be connected to a lead extension or directly to the control module 102 through terminals 122, and the distal end 108 has the electrodes 104 disposed thereon.

Figure 3A:
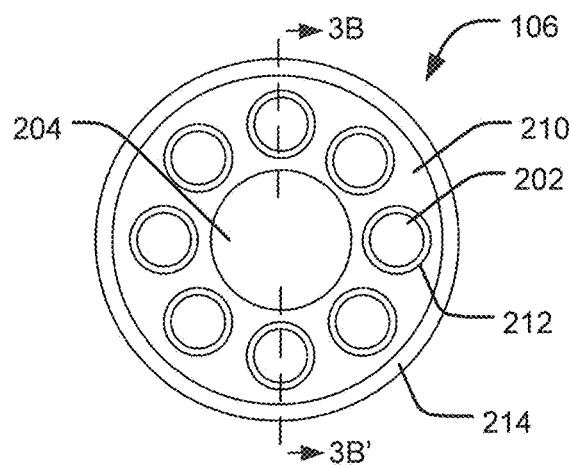
FIG. 3A is a schematic lateral cross-sectional view of the lead of FIG. 1, taken on plane 3A-3A', according to the invention.
Figure 3B:
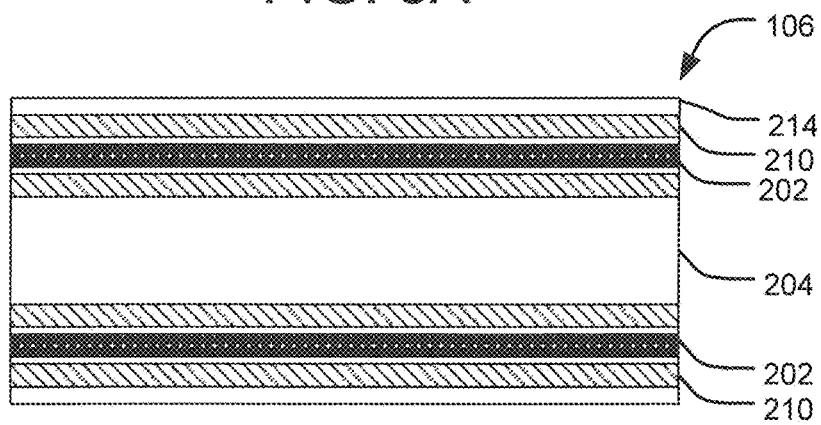
FIG. 3B is a schematic longitudinal cross-sectional view of the lead of FIG. 3A taken on plane 3B-3B', according to the invention.
Figure 3C:
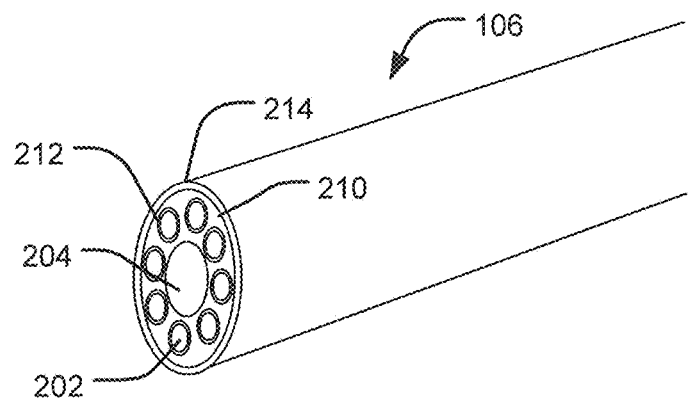
FIG. 3C is a schematic perspective view of the lead of FIG. 1 cut at 3A-3A', according to the invention.

FIG. 3A is a cross-sectional view of lead 106 taken along line 3A-3A' in FIG. 1, FIG. 3B is a cut-away sectional side view taken along line 3B-3B', and FIG. 3C is a perspective view of the lead 106 cut at line 3A-3A' in FIG. 1. In this embodiment, the lead 106 includes one or more conductors 202, each of which may be separately covered by its own insulated outer sheath or covering. At their proximal ends, the conductors are coupled to the terminals 122 for connecting the lead to the connector 118, and at their distal ends, the conductors 202 are coupled to the electrodes 104. For example, the lead 106 may include as many conductors as electrodes, and each conductor 202 may be connected to a different electrode 104 and a different terminal. This arrangement allows the control module 102 to individually control stimulation provided to each electrode 104. Alternatively, two or more electrodes may be connected to the same conductor 202 such that electrical stimulation to these electrodes is provided simultaneously.

Figure 2:
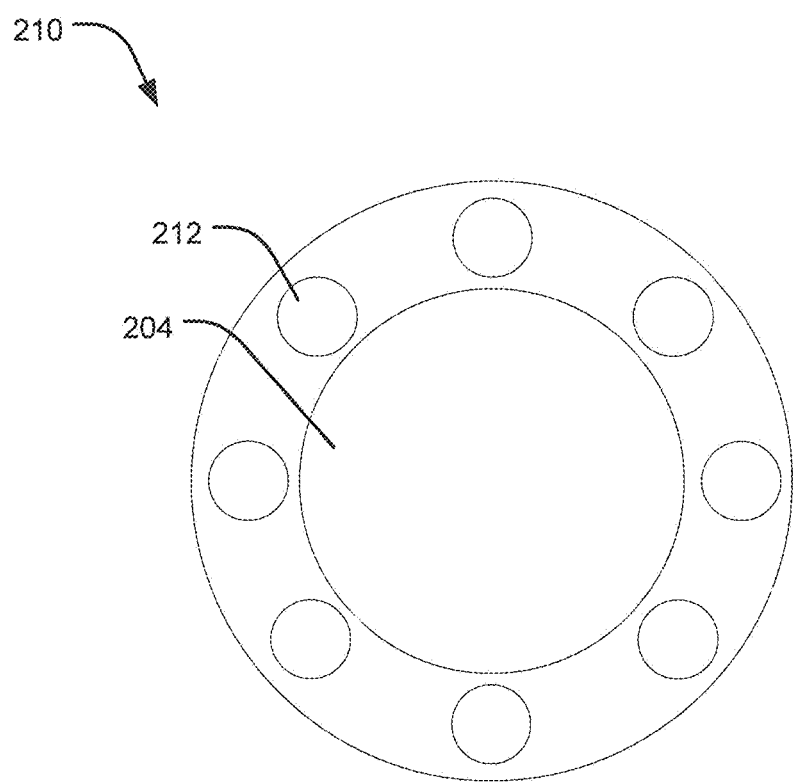
FIG. 2 is a schematic lateral cross-sectional view of one embodiment of a multilumen tube, according to the invention.

In the embodiment of FIG. 3A, the lead includes a non-conductive multilumen tube 210 through which the conductors 202 pass. FIG. 2 illustrates one embodiment of a multilumen tube 210. The multilumen tube 210 may include one or more conductor lumens 212. The multilumen tube 210 may further include an inner stylet lumen 204 running through at least a portion of the length of the lead. This lumen may have an opening at its proximal end to permit the insertion of a stylet, which stiffens the lead so that an operator may easily insert and steer the lead during implantation into the patient's body.

The conductors 202 may be embedded in the non-conductive material of the lead, or they can be disposed in one or more lumens extending along the lead as described above. Some embodiments provide an individual lumen for each conductor. In other embodiments, two or more conductors may extend through each lumen. Additionally, one or more lumens (not shown) may open at, or near, the distal end of the lead, permitting infusion of drugs or medication into implantation. Optionally, some or all lumens may be flushed continually, or on a regular basis, with saline, epidural fluid, or the like. Moreover, the lumens may be permanently or removably sealable at the distal end.

An optional exterior cover 214 and the multilumen tube 210 can be formed of a non-conductive, biocompatible material including, for example, silicone, polyurethane, or polyetheretherketone ("PEEK"). The multilumen tube 210 and exterior cover 214 of the lead 106 may be formed in the desired shape by any suitable process including, for example, molding (including injection molding), casting, or extrusion. Electrodes and conductors can be disposed onto or within the lead either during or after a molding or casting process. The non-conductive material typically extends from the distal end of the lead to its proximal end. Moreover, the material of the multilumen tube and the exterior cover may be the same or different, and the multilumen tube and the exterior cover may be a unitary structure or formed as two separate structures that are permanently or detachably coupled.

In at least some embodiments, the lead 106 has a reduced outer diameter relative to conventional leads with the outer diameter being no more than 0.040", 0.039", 0.035", 0.030", 0.027", or 0.022" (approximately, 1, 0.99, 0.89, 0.76, 0.69, or 0.56 mm, respectively). This outer diameter is provided at least along the electrode-bearing portion of the lead. In at least some embodiments, the lead is isodiametric. In other embodiments, portions of the lead may have a wider diameter, such as a terminal-bearing portion of the lead. This particular arrangement may be desirable so that the terminal-bearing portion of the lead can be inserted into conventional connectors on a control module or lead extension.

In this particular embodiment, the lead has a multilumen tube 210 with eight equidistant conductor lumens 212 and a stylet lumen 204. The lumens 212 run along the length of the lead 106, while the stylet lumen 204 may run along at least a portion of the lead's length.

Conductors 202, such as solid, single strand wires or multi-strand braided cable conductors, may be inserted in the lumens 212 to provide electrical connection between the control module 102 and the electrodes 104. In one embodiment, the diameter of the lead 106 is about 0.039" (approximately 0.99 mm). To achieve this diameter, each lumen 212 is approximately 0.008" (approximately 0.2 mm) wide, and the stylet lumen 204 diameter is about 0.016" (approximately 0.4 mm). This construction allows the employment of cable conductors 202 having diameters approximately equal to 0.005" (approximately 0.13 mm) and stylets with diameters approximately equal to 0.014" (approximately 0.36 mm). It will be understood that the number of lumens 212 and their placement may vary according to specific requirements. For example, if the stimulation system 100 includes four electrodes 104, the number of lumens 212 may be reduced to four. Similarly, if the stimulation system 100 includes ten electrodes, the number of lumens 212 may increase. Moreover, multiple conductors may be disposed in the one lumen, further decreasing the lead diameter. To incorporate more lumens, the size of each lumen 212 may be decreased further. For example, the lumen size may be reduced to a value between about 0.002"-0.005" (approximately 0.05 to 0.13 mm).

In at least some embodiments, the conductors 202 can be multi-strand cable conductors instead of single wire solid conductors because multi-strand conductors often exhibit greater flexibility and lower flex fatigue than solid conductors.

In one method of manufacture, the conductors are threaded through the lumens of the multilumen tube. An outer portion of the multilumen tube may be removed (by ablation or any other suitable technique) on both ends of the lead. For example, any suitable ablation technique may be utilized, such as laser, chemical, or thermal ablation. Moreover, abrasive techniques, such as eroding or cutting, or mechanical techniques, such as skiving, may alternately be employed.

Contact terminals, electrodes, and spacers with diameters in excess of 0.035" may be fitted over ablated end of the multilumen tube and the ends of the conductors can be coupled to the terminals and electrodes. For example, the electrodes and contacts may be welded, soldered, or adhesively adhered (using a conductive adhesive) onto the ends of the conductors. Optionally, reflow or backfill techniques may be used to partially or completely fill in the ends of the lumens and to lock the electrodes and terminals in place after coupling the conductors to the terminals and electrodes. In another method, overmolding or casting may be employed to lock the electrode and terminal arrays in place.

Subsequently, to smooth over the outer surface of the lead and to further reduce the diameter marginally, the outer surface may be polished or ground. For instance, the final lead diameter may result from, for example, centerless grinding.

In another embodiment, the multilumen tube can be extruded with the conductors in place and extending along the tube. In this method, the conductor lumens can be smaller because they do not need to accommodate threading the conductors through the lumens. The conductor lumens can be coextensive with (e.g., have the same diameter as) the conductors themselves. After the extrusion, portions of the multilumen tube can be removed (e.g., by ablation) to expose the ends of the conductors for attachment of the terminals and electrodes at the respective ends of the lead.

To easily steer or guide the lead through cavities in the patient's body, the lead may be coated with a lubricious material. Moreover, an antibiotic agent may be coated on the lead's outer surface to prevent any infections in tissues around the lead.

The diameter of the lead may be uniform throughout its length. Alternatively, the lead's diameter may be less or more at the distal end, as compared to the rest of the lead body; or, the diameter may be less or more at the proximal end, as compared to the rest of the lead body. In one embodiment, the distal end, which is present at the target side, may have a smaller diameter as compared to the end coupled to the control module. Such small diameter lead may be easily used to stimulate areas where the overlying tissue is thin, such as the face or other subcutaneous locations. Moreover, by employing a wider proximal end conventional control modules may be utilized without any design modifications.

Figure 4:
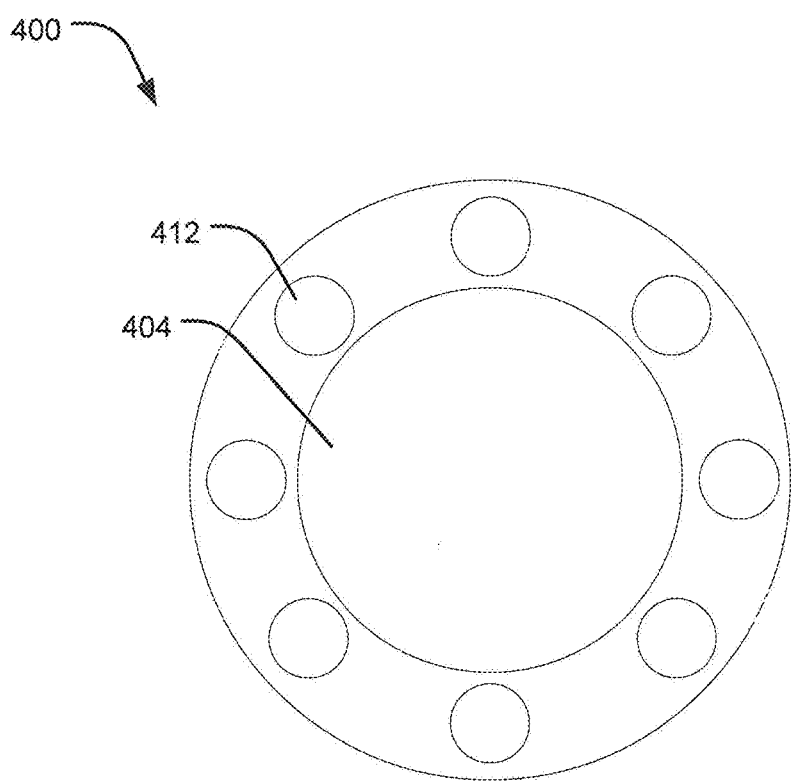
FIG. 4 is schematic lateral cross-sectional view of another embodiment of a multi-lumen tube for use in a lead, according to the invention.

FIG. 4 illustrates another embodiment of a lead 400. The diameter of the lead 400 is reduced to approximately 0.027" (approximately, 0.69 mm). The design includes a central stylet lumen 404 ranging from 0.012"-0.016" (about 0.3 to 0.4 mm), and conductor lumens 412 ranging from 0.003" to 0.005" (about 0.07 to 0.13 mm). The diameter of the stylet lumen 404 and the conductor lumens 412 is optimized to achieve acute steerability and chronic fatigue resistance. This lead 400 may also be manufactured using any of the methods described in relation to the embodiments illustrated in FIGS. 3A-3C.

Figure 5:
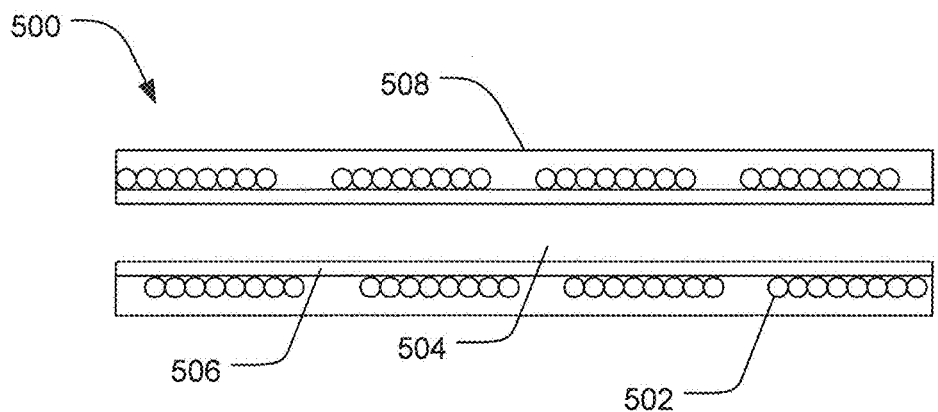
FIG. 5 is a schematic longitudinal cross-sectional view of a portion of an embodiment of a lead with wrapped conductors, according to the invention.

FIG. 5 illustrates yet another embodiment of a small diameter lead 500. Instead of a multilumen construction, a multifilar coil construction is utilized. Multiple conducting wires form a multifilar coil 502 that is coiled around the central stylet lumen 504 and extends longitudinally from the proximal end 110 to the distal end 108 of the lead. As one example, a stimulation system 100 with eight electrodes and eight terminals can have eight conducting wires that form an eight-wire multifilar coil coiled around the central stylet lumen 204 and extending from the terminals at the proximal end of the lead to the electrodes at the distal end of the lead. The distal end of each wire of the multifilar coil 502 is coupled to at least one electrode and the proximal end of the each wire is coupled to at least one terminal 120. Each conductor may be coated with an insulative material, such as polyurethane to prevent any electrical connection between adjacent wires. The wires of the multifilar coil can be arranged in a single layer as illustrated in FIG. 5.

The conductors, or filars, in the multifilar coil 502 may be constructed from a conductive low resistance material such as MP35N or DFT (drawn filled tubes). These materials provide high flexibility to the multifilar coil 502 and resistance to breakage. Therefore, these coils may be utilized in the reduced diameter lead design. Each filar may be individually insulated from one another and wound together.

To construct this lead, the conductor coil 502 may be wound around a protective insulator 506 that defines stylet lumen 504. During manufacture, a mandrel may be disposed in the stylet lumen. As one example, a 0.016" (approximately 0.4 mm) lumen may be provided for a stylet. An insulative material 508 may be disposed over the wound conductor coil and then optionally reflowed. Once the insulative material solidifies, the excess insulative material may be removed by ablation, grinding, skiving, or any other suitable technique. Centerless or centered grinding may be performed to further smooth the outer surface of the lead and further reduce the diameter of the lead. Using this procedure, leads with diameters approximately equal to 0.030" or less (approximately 0.76 mm) may be obtained.

The exemplary leads illustrated in FIGS. 3-5 may have lead diameters between, for example, 0.039" to 0.027" (approximately, 1 mm to 0.69 mm). To obtain leads of even smaller diameter, the stylet lumen may be removed. In case of deep implantation, these leads may be steered to the target area using steerable catheters or endoscopic devices. In peripheral applications, however, an external steering mechanism or device may not be required as the electrodes 104 are implanted close to the incision location.

Figure 6:
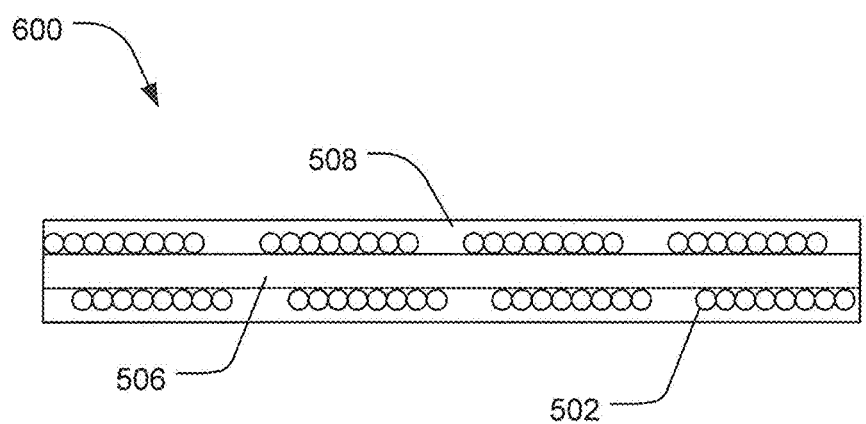
FIG. 6 is a schematic longitudinal cross-sectional view of a portion of another embodiment of a lead with wrapped conductors, according to the invention.

FIG. 6 illustrates an embodiment of a reduced diameter lead 600 without a stylet lumen. Here, the diameter of the insulator 506 may be smaller than that of the insulator described with reference to FIG. 5. The construction and design of this embodiment is similar to the construction and design of the lead described with reference to FIG. 5, and therefore those details will not be described further.

Figure 7:
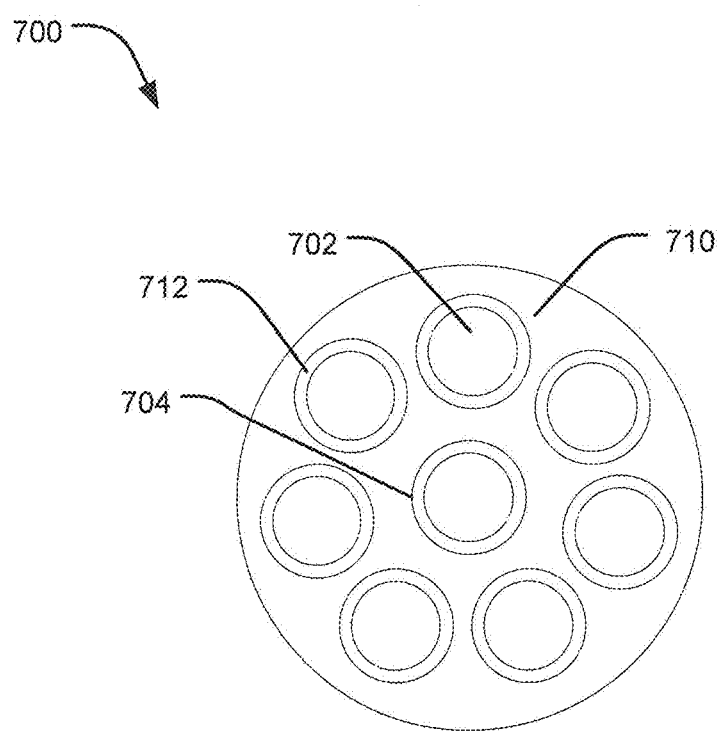
FIG. 7 is a schematic lateral cross-sectional view of another embodiment of a lead, according to the invention.

FIG. 7 illustrates an embodiment of a reduced diameter lead 700 with multilumen tube 710 construction, but without a stylet lumen. The multilumen tube 710 includes a central lumen 704 and at least seven peripheral lumens 712 arranged circumferentially around the central lumen. Here, because the central lumen 704 is not utilized for a stylet, one or more conductors 702 may be passed through it. Active use of the central lumen reduces the number of surrounding lumens, further reducing the diameter of the lead 700. With this design, diameters of approximately 0.022"-0.035" (approximately 0.56 to 0.89 mm) or better may be achieved. If the number of electrodes at the distal end of the lead 700 is reduced, the lead diameter may further decrease correspondingly. The construction of this embodiment is similar to the construction of the multilumen lead described with reference to FIGS. 3A-3C. This lead may include an optional external cover similar to that illustrated in FIG. 3A The reduced diameter leads described herein may be utilized in numerous applications. For instance, the reduced diameter leads may be implanted in targets where the tissue above covering the lead, under skin, is very thin. Such target areas include areas on the face such as above the eyebrows for treatment of suborbital pain, on the trigeminal nerve for treatment of facial pain and potentially epilepsy, on the skull for treatment of migraine, in the limbs for treatment of local peripheral pain. Standard diameter leads may be aesthetically unsuitable in these areas as the lead may be visible under the skin. Additionally, the reduced diameter leads may be useful for underweight patients.

The small diameter leads may also be beneficial in the area of deep brain stimulation as the cannula and tract made for the small diameter lead could be significantly smaller in diameter, displacing less brain tissue, and reducing any possible brain damage.

A lead with low profile electrodes may be particularly useful where space is limited, for example, around the skull or face. When a lead is too large for the intended target, issues such as patient discomfort, skin erosion, or visible distortion of the skin over the electrode array may arise.

A lead with a distal portion, including at least the electrode array (or a portion of the electrode array), can be formed with a lower profile by reducing the diameter of the distal portion of the lead in one direction while preferably maintaining the original lead diameter in the orthogonal direction. Such arrangements can provide a lead with, for example, an oval, elliptical, or rectangular lateral cross-section. Such leads may be particularly well suited for stimulation on or around the skull, such as occipital nerve stimulation for headache, or on or around the face, such as orbital nerve stimulation for eye socket pain. The lead could also be used for spinal cord stimulation in the epidural space, particularly where the epidural space may be small due to, for example, extensive fibrotic or scar tissue or where narrowing has occurred due to, for example, prior surgery or other implanted hardware.

Figure 8A:
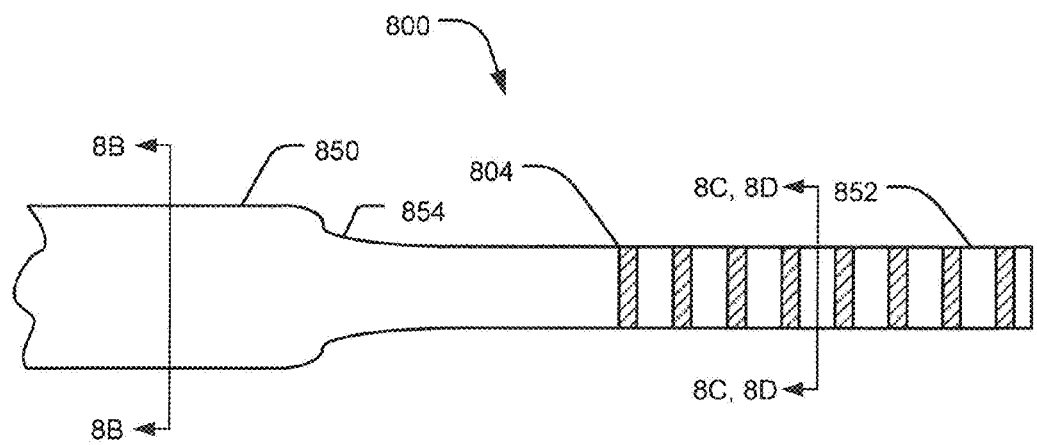
FIG. 8A is a schematic longitudinal cross-sectional view of a distal portion of an embodiment of a lead with a low-profile region, according to the invention.
Figure 8B:
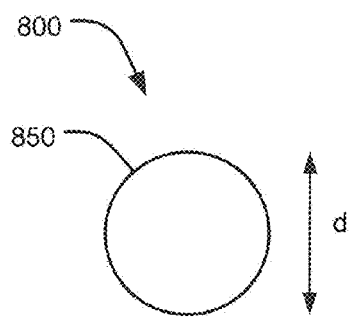
FIG. 8B is a schematic lateral cross-sectional view of a portion of the lead of FIG. 8A, according to the invention.
Figure 8C:
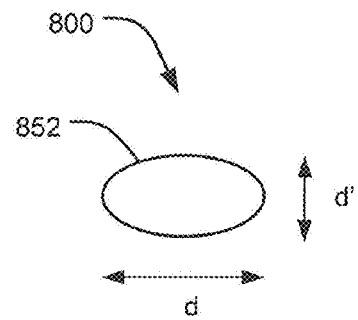
FIG. 8C is a schematic lateral cross-sectional view of one embodiment of the low-profile region of the lead of FIG. 8A, according to the invention.
Figure 8D:
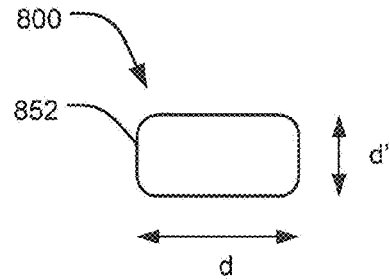
FIG. 8D is a schematic lateral cross-sectional view of a second embodiment of the low-profile region of the lead of FIG. 8A, according to the invention.

FIG. 8A is a side view of the distal portion of a lead 800 with a region 850 having a circular lateral cross-section, illustrated in FIG. 8B, and a low-profile region 852 with a low profile cross-section, such as either of the lateral cross-sections illustrated in FIGS. 8C and 8D. Between these two regions 850, 852 is a transition region 854. For example, the lateral cross-section of the low-profile region 852 in FIG. 8C is an oval and the lateral cross-section of the low profile region 852 in FIG. 8D is rectangular. It will be recognized that other non-circular cross-sections can also be used.

The low-profile region 852 in the embodiments of FIGS. 8A-8D includes all of the electrodes 804. In some embodiments, the low-profile region 852 will also include a portion of the lead immediately proximal to the electrodes 804. That portion (proximal to the electrodes and within the low-profile region) may have a length, for example, at least 25%, 50%, 100%, 200%, 300%, or more of the length of the portion of the lead containing the electrodes. In other embodiments, the low-profile region may only contain some (for example, no more than 90%, 75%, 50%, or 25%) of the electrodes of the lead. The remaining electrodes may be in the transition region 854 or region 850 (or any combination thereof) of the lead.

In at least some embodiments, the region 850 of the lead has a relatively uniform diameter, d, as illustrated in FIG. 8B. The low-profile region 852 may have the diameter, d, in one direction and a smaller diameter, d', in an orthogonal direction, as illustrated, for example, in FIGS. 8C and 8D. The smaller diameter d' may be no more than 90%, 80%, 75%, 60%, 50%, 40%, 33%, or 25% or less than the diameter d of region 850.

Figure 9:
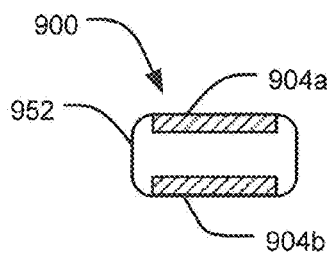
FIG. 9 is a schematic lateral cross-sectional view of a low-profile region of a lead with segmented electrodes, according to the invention.

In FIGS. 8A-8D, the electrodes 804 are depicted as extending around the entire circumference of the lead. It will be understood that other electrode arrangements can be used including segmented electrode arrangements where the segmented electrodes extend around less than the entire circumference of the lead and, in some embodiments, multiple segmented electrodes may be presented at the same longitudinal position, but different circumferential positions, on the lead. One example is presented in FIG. 9 which is a lateral cross-section of the low-profile region 952 of a lead 900 taken through two opposing electrodes 904a, 904b that are disposed on opposing surfaces of a low-profile region having a rectangular cross-section. It will be understood that such electrodes can be formed on low-profile regions with oval, elliptical, or any other cross-section. Examples of segmented electrodes and their formation can be found in, for example, U.S. Patent Application Publications Nos. 2011/0005069, 2010/0268298-A1, 2011/0238129-A1, 2012/0016378-A1, 2011/0130817-A1, 2011/0130816-A1, 2011/0130818-A1, 2011/0130803-A1, 2011/0313500-A1, 2012/0046710-A1, 2012/0071949-A1, 2011/0078900-A1, 2012/0165911-A1, 2012/0197375-A1, 2012/0203320-A1, 2012/0203321-A1, and 2012/0203316-A1, all of which are incorporated herein by reference. It will be understood that the segmented electrode arrangements described in these references can be adapted to the non-circular, low-profile regions described herein.

While the present disclosure has been described by means of specific embodiments and applications thereof, numerous modifications and variations could be made thereto by those skilled in the art without departing from the scope of the present disclosure set forth in the claims.

What is claimed is:

1. A stimulation lead having a proximal portion and a distal portion, the stimulation lead comprising:
    an elongate body having a proximal portion and a distal portion;
    a plurality of terminals disposed along the proximal portion of the elongate body;
    a plurality of electrodes disposed along the distal portion of the elongate body; and
    a plurality of conductors coupling the plurality of terminals to the plurality of electrodes,
    wherein the proximal portion of the stimulation lead has a circular lateral cross-section with an outer diameter and the distal portion of the stimulation lead comprises a low-profile region in which the stimulation lead has a non-circular lateral cross-section with an outer diameter that is no greater than the outer diameter of the circular lateral cross-section in any direction and, in at least one direction, is at least 10% less than the outer diameter of the circular lateral cross-section, wherein the plurality of electrodes are disposed in a portion of the low-profile region, wherein the outer diameter of the low-profile region of the stimulation lead with the non-circular lateral cross-section is no more than 0.039" in any direction and is constant in at least the portion in which the electrodes are disposed.

2. The stimulation lead of claim 1, wherein the stimulation lead in the low profile region has an oval, elliptical, or rectangular cross-section.

3. The stimulation lead of claim 1, wherein the low-profile region has a circumference and each of the electrodes extends entirely around the circumference of the low-profile region.

4. The stimulation lead of claim 1, further comprising a multilumen tube extending along the elongate body and defining a central lumen and a plurality of peripheral lumens disposed circumferentially around the central lumen.

5. The stimulation lead of claim 4, wherein at least one of the plurality of conductors extends along the central lumen and a remainder of the plurality of conductors extend along the plurality of peripheral lumens with at least one of the plurality of conductors in each peripheral lumen.

6. The stimulation lead of claim 1, wherein the stimulation lead has an outer diameter of no more than 0.039" except along the proximal portion of the stimulation lead.

7. The stimulation lead of claim 4, wherein the multilumen tube defines at least seven peripheral lumens.

8. The stimulation lead of claim 7, wherein each peripheral lumen, as well as the central lumen, has a single one of the conductors extending therein and wherein each conductor is coupled to a different terminal and a different electrode.

9. The stimulation lead of claim 1, wherein each of the conductors is a multi-strand cable conductor.

10. The stimulation lead of claim 1, wherein the elongate body comprises an insulative core extending from the proximal portion to the distal portion of the elongate body.

11. The stimulation lead of claim 10, wherein the plurality of conductors comprises at least eight conductors extending along the elongate body and collectively wrapped around the insulative core, the conductors being electrically insulated from each other.

12. The stimulation lead of claim 11, wherein the at least eight conductors are wrapped in a single layer around the insulative core.

13. The stimulation lead of claim 10, wherein the insulative core defines a central lumen.

14. The stimulation lead of claim 1, wherein an outer diameter of the lead is no more than 0.030" in any direction along at least a portion of the lead containing the electrodes.

15. The stimulation lead of claim 1, wherein an outer diameter of the lead is in a range of 0.025"-0.027" in any direction along at least a portion of the lead containing the electrodes.

16. The stimulation lead of claim 1, wherein the non-circular lateral cross-section is an oval cross-section with an outer diameter in a first direction equal to the outer diameter of the circular lateral cross-section and an outer diameter in a second direction, perpendicular to the first direction, that is at least 10% less than the outer diameter of the circular lateral cross-section.

* * * * *